US008944814B2

(12) United States Patent
Mossle

(10) Patent No.: US 8,944,814 B2
(45) Date of Patent: Feb. 3, 2015

(54) HAND APPARATUS, IN PARTICULAR FOR DENTAL PURPOSES, FOR DISPENSING A PASTY FILLER MASS

(75) Inventor: Walter Mossle, Mittelbiberach (DE)

(73) Assignee: Kaltenbach & Voigt GmbH, Biberach (DE)

( * ) Notice: Subject to any disclaimer, the term of this patent is extended or adjusted under 35 U.S.C. 154(b) by 0 days.

(21) Appl. No.: 13/270,303

(22) Filed: Oct. 11, 2011

(65) Prior Publication Data

US 2012/0028216 A1 Feb. 2, 2012

Related U.S. Application Data

(62) Division of application No. 11/993,968, filed as application No. PCT/EP2006/005973 on Jun. 21, 2006.

(30) Foreign Application Priority Data

Jun. 22, 2005 (DE) ......................... 10 2005 028 925

(51) Int. Cl.
*A61C 5/06* (2006.01)
*B05C 17/005* (2006.01)
*A61C 1/07* (2006.01)
(Continued)

(52) U.S. Cl.
CPC ............. *B05C 17/00593* (2013.01); *A61C 1/07* (2013.01); *A61C 3/03* (2013.01); *A61C 5/04* (2013.01); *A61C 5/062* (2013.01); *A61C 9/0026* (2013.01); *A61C 17/20* (2013.01)
USPC .......................................................... 433/118

(58) Field of Classification Search
USPC ........... 433/29, 88, 89, 81, 82, 85, 87, 90, 80, 433/118, 119; 222/196, 196.1–196.5, 222/197–203
See application file for complete search history.

(56) References Cited

U.S. PATENT DOCUMENTS 3,792,530 A 2/1974 Smith
3,890,713 A 6/1975 Nielsen
(Continued)

FOREIGN PATENT DOCUMENTS

DE 29517958 3/1997
DE 10001513 4/2001
(Continued)

OTHER PUBLICATIONS

Certification and Certified translation of PCT application PCT/EP2006/005973.

(Continued)

*Primary Examiner* — Ralph Lewis
(74) *Attorney, Agent, or Firm* — Neifeld IP Law, PC

(57) ABSTRACT

The invention concerns a hand apparatus (1), in particular for dental purposes, for dispensing a pasty filler mass (M) the viscosity of which can be reduced by supplying vibration energy, having an apparatus housing (5), having a container (4) for the pasty filler mass (M), having an exit nozzle (11) standing in connection with the container (4), having a vibration generator (3), and having pressure production means (18) for exercising pressure on the pasty filler mass (M). In order to improve the transfer of vibrations in the region of the of the hand apparatus the vibration generator (3) and the container (4) are mounted movably with respect to the apparatus housing (5) and are directly vibration-coupled with each other.

9 Claims, 4 Drawing Sheets

Figure 1:
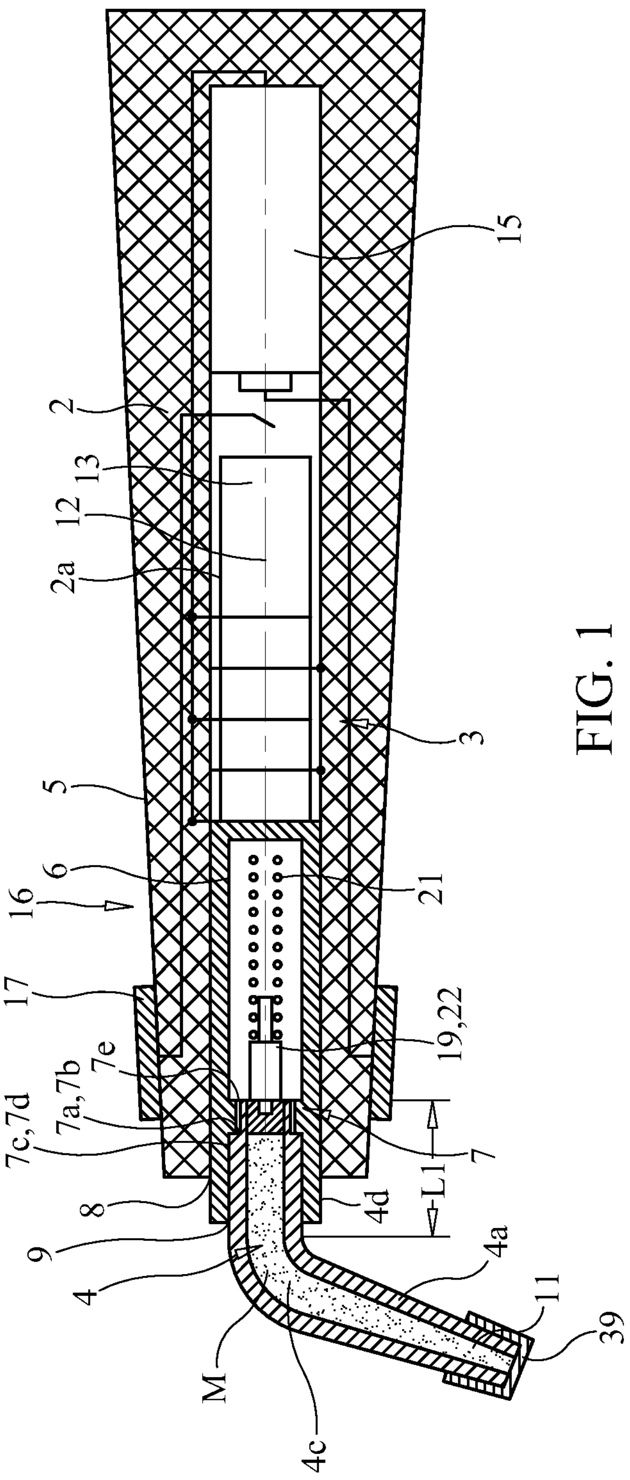

(51) Int. Cl.

| | |
|---|---|
| ***A61C 3/03*** | (2006.01) |
| ***A61C 5/04*** | (2006.01) |
| ***A61C 9/00*** | (2006.01) |
| *A61C 17/20* | (2006.01) |

(56) References Cited

U.S. PATENT DOCUMENTS

| | | | | |
|---|---|---|---|---|
| 4,092,778 | A | | 6/1978 | Hirdes |
| RE29,687 | E | | 7/1978 | Sertich |
| 4,330,282 | A | | 5/1982 | Nash |
| 4,673,353 | A | | 6/1987 | Nevin |
| 4,768,955 | A | * | 9/1988 | Hirdes ............................ 433/89 |
| 5,015,237 | A | | 5/1991 | Kleinwolterink, Jr. et al. |
| 5,083,921 | A | | 1/1992 | Dragan |
| 5,125,837 | A | | 6/1992 | Warrin et al. |
| 5,195,663 | A | | 3/1993 | Martin et al. |
| 5,232,363 | A | | 8/1993 | Meller |
| 5,244,933 | A | | 9/1993 | Eidenbenz et al. |
| 5,908,295 | A | | 6/1999 | Kawata |
| 6,305,934 | B1 | | 10/2001 | Hatley, Jr. |
| 6,375,039 | B1 | | 4/2002 | Anderson |
| 6,848,906 | B2 | | 2/2005 | Albach |
| 7,014,462 | B1 | | 3/2006 | Tilse |
| 7,857,621 | B2 | | 12/2010 | Teufelberger et al. |
| 2002/0123020 | A1 | | 9/2002 | Aumuller et al. |
| 2003/0152886 | A1 | | 8/2003 | Houdt |
| 2004/0152041 | A1 | | 8/2004 | Metzbower |
| 2005/0026106 | A1 | | 2/2005 | Jefferies |
| 2006/0019220 | A1 | | 1/2006 | Loebel et al. |
| 2008/0206706 | A1 | | 8/2008 | Mossle |

FOREIGN PATENT DOCUMENTS

| | | | | |
|---|---|---|---|---|
| DE | 10 2005 028925.8 | | | 7/2006 |
| DE | 8904429 | | | 11/2009 |
| EP | 0480472 | | | 10/1991 |
| FR | 2190176 | | | 3/1974 |
| FR | 2199965 | | | 4/1974 |
| WO | WO 0117454 | | | 3/2001 |
| WO | WO 2004/082508 | | | 9/2004 |
| WO | WO 2004082508 | A1 | * | 9/2004 |
| WO | WO 2006/013698 | | | 12/2006 |

OTHER PUBLICATIONS

Certification and Certified translation of German priority application DE 10 2005 028 925.8.

International Search Report for PCT/EP2006/005973 dated Mar. 21, 2007.

International Search Report for PCT/EP2006/005973 dated May 18, 2007.

International Preliminary Report on Patentability for PCT/EP2006/005973 dated Feb. 5, 2008.

Google generated English translation for WO 0117454, also cited herewith as reference F-005.

Sep. 28, 2011 letter from Clemens Thun to Rick Neifeld.

Cover page of German priority application DE 10 2005 028 925.8.

Certification and Certified translation into English of PCT application PCT/EP2006/005973.

Certification and Certified translation into English of German priority application DE 10 2005 028 925.8.

Certification and Certified translation of p. 14 line 38 to p. 15 line 23 of WO 2006/136398 publication of PCT application PCT/EP2006/005973.

European Search Report for EP06027381.

European Search Report for EP06027382.

Inernational Search Report for PCT/EP2006/005973 dated Mar. 21, 2007.

Cover page of Certified German priority application DE 10 2005 028 925.8.

Mar. 30, 2007, European Search Report for EP06027381.

Mar. 30, 2007, European Search Report for EP06027382.

May 12, 2014, Decision—Motions—37 CFR § 41.125(a) in Patent Interference 105.934, Related U.S. Appl. No. 11/993,968, Inventor Mossle.

May 12, 2014, Redeclaration—37 CFR § 41.203(c) in Patent Interference 105.934, Related U.S. Appl. No. 11/993,968, Inventor Mossle.

May 12, 2014, Judgment—Priority—37 CFR § 41.127 in Patent Interference 105.934, Related U.S. Appl. No. 11/993,968, Inventor Mossle.

May 12, 2014, Decision—Motions—37 CFR § 41.125(a) in Patent Interference 105.962, Related U.S. Appl. No. 13/270,303, Inventor Mossle.

May 12, 2014, Redeclaration—37 CFR § 41.203(c) in Patent Interference 105.962, Related U.S. Appl. No. 13/270,303, Inventor Mossle.

May 12, 2014, Judgment—Priority—37 CFR § 41.127 in Patent Interference 105.962, Related U.S. Appl. No. 13/270,303, Inventor Mossle.

* cited by examiner

HAND APPARATUS, IN PARTICULAR FOR DENTAL PURPOSES, FOR DISPENSING A PASTY FILLER MASS

This application is a division of application Ser. No. 11/993,968, which has a 371 completion date of Mar. 11, 2008, which is the U.S. national stage entry of international application PCT/EP2006/005973, filed Jun. 21, 2006, which claims priority to DE 10 2005 028 925.8, filed Jun. 22, 2005. The entire contents of application PCT/EP2006/005973 is incorporated herein by reference.

The invention relates to a hand apparatus in accordance with the preamble of claims 1 to 5 and to a container for such a hand apparatus.

In medical technology it is known to fill, and therefore to repair, cavities in an animal or human body part or in a prosthesis with a filler material, e.g. after material removing working of a defect. For this, curable filler masses are used, which are brought into the cavity in a pasty or liquid condition and then harden. Thereby, a distinction is to be made between a direct filling and an indirect filling. In a direct filling only the filler mass is brought into the cavity, so that it fills the cavity. In an indirect filling a preferably customized inlay placement part is put in place in the cavity with the filler mass, so that the latter connects the placement part with the wall of the cavity. Here, not only is a mechanical anchorage of the filler mass in the cavity important, but also a sealed placement of the filler mass in the cavity, to avoid gaps through which contaminants and germs, which in the case of a body tissue could lead to inflammation and which could destroy the preparation, could penetrate.

A typical application of an above-described preparation, in which there arise particular requirements regarding the hand apparatus and the handling thereof, is tooth preparation in the mouth of a patient or a training head for teaching purposes. With such a dental-medical treatment case there arise particular requirements regarding the structural size of the handpiece, since the mouth of a patient is relatively small, and therefore under consideration of a required freedom of view a structural size as small as possible is to be striven for.

In DE 100 01 513 A1 there are described a method of filling a tooth filler mass, based on synthetic resin, into a cavity of a tooth, and a hand apparatus for carrying out such a method, wherein during filling the filler mass and a nozzle of the hand apparatus are acted upon with sound, particular with ultrasound, and the hand apparatus has means which convey the filler mass from a supply container of the nozzle. This known method and hand apparatus made it possible to use filler masses with a relatively high content of fillers, which increase the toughness of the filler mass and thereby reduce shrinkage and the danger of gap formation upon hardening. With this known hand apparatus a lever arrangement is provided for conveying the filler mass, which upon its manual actuation at the same time switches on an ultrasound source, in particular a piezo-oscillator, which is arranged in the rearward region of the hand apparatus body. The filler mass is arranged in a cartridge which can be put in place and fixed in a section arranged in the forward end region of the hand apparatus body. Upon manual actuation of the lever arrangement the filler mass is conveyed out by an advancing punch connected to the lever arrangement and acting on the rearward end of the cartridge.

From EP 0 480 472 B1 there can be understood a method for the production of dental masses which contain a binder or such a high proportion of filler materials, that the dental mass itself is not usable for the intended purpose due to its high viscosity, whereby however one mixes the filler materials with the binder under the action of an oscillation in the frequency range 20 Hz to 50 kHz with an amplitude of 1 μm to 5 μm, through which the viscosity is reduced to a usable value.

The invention is based on the object, with a hand apparatus in accordance with the preamble of the claim 1, of improving vibration transmission in the region of the hand apparatus.

This object is achieved by the features of claim 1 or 2. Advantageous developments of the invention are indicated in the dependent claims.

The invention is based on the insight that the handpiece apparatus body is only poorly suited for transferring the vibrations provided by the vibration generator to the container or the filler mass.

In accordance with the configuration in accordance with the invention according to claim 1, the vibration generator and the container are mounted movably with respect to the apparatus housing and directly vibration-coupled with each other.

In accordance with the configuration in accordance with the invention according to claim 2 there extends forwardly from the vibration generator a vibration part vibration-coupled therewith, which is mounted axially and/or radially or 3-dimensionally oscillatable in the apparatus housing, and has a receiving chamber, accessible from the front, for the container or the filler mass has.

Both in the case of the configuration in accordance with the invention according to claim 1 and also that according to claim 2 the apparatus housing is not a component directly transferring the vibrations, and it is therefore largely free from vibration transmission. Through this, the vibration energy applied by the vibration generator can be better transferred to the container and the filler mass. This is possible in that the vibration generator, the container and the oscillation part is mounted in the apparatus housing movably or oscillatably and therefore only a relatively slight part of the vibration power is transferred to the apparatus housing, whereby this part is determined by the preferably elastic mounting function, with which a slight part of the vibration energy—at least with radial or 3-dimensional oscillation amplitudes—is inevitably transferred to the apparatus housing. The apparatus housing is therefore largely freed from the vibration transmission. Through this the hand apparatus in accordance with the invention is also handling friendly because upon handling hardly any vibrations are transferred to the operating hand gripping the hand apparatus.

Within the scope of the invention the oscillation part may be connected vibration-coupled to the container for the filler mass, or it may have a receiving chamber, accessible from the fore, for the filler mass. Insofar as a container is present, this can project into the receiving chamber completely or only with its rearward region.

To ensure a loss as slight as possible of the vibration energy upon the transmission of the vibrations from the oscillation part to the container, it is advantageous to so connect the container with the oscillation part by means of a connection so firm that a vibration coupling is present between the container and the oscillation part and also the vibration generator, which due to the direct transmission makes possible the desired great usage of the vibration energy. This can be realized e.g. in that the connection is formed by a screw connection and/or in that the container bears, with a peripheral surface, on an inner peripheral surface of the oscillation part.

The invention is further based on the object of so configuring a hand apparatus in accordance with the preamble of the claim 3 that its filling function is improved.

This object is achieved by the features of the claim 3.

With the configuration in accordance with the invention according to claim 3 there is provided a setting means for adjusting the vibration energy to be transferred to the container.

This configuration in accordance with the invention is based on the insight that by action on the container with differently large vibration energies differently large viscosities are achieved, which in operation lead to differently large quantities of filler mass leaving the exit nozzle. Thereby the invention is further based on the insight that the differently large exit quantities are suitable for differently large cavities to be filled and therefore the configuration in accordance with the invention not only not makes the hand apparatus more efficient with regard to a desired exit quantity because selectively great and small exit quantities can be selected, but also makes possible adaptability to different filling requirements. For filling small cavities or cavities of difficult form the hand apparatus in accordance with the invention can be adjusted for the dispensing of a small filling mass quantity and for large cavities for the dispensing of a great filling mass quantity. The selectively adjustable greater or smaller dispensing quantity can be effected in at least one step or in stepless manner.

The invention is based further on the object of simplifying a hand apparatus in accordance with the preamble of claim 4 with regard to its drive.

This object is achieved by the features of the claim 4. Advantageous developments of the invention are indicated in the associated dependent claims.

Regarding the configuration according to claim 4 the invention is based on the insight that two drive functions are present, namely on the one hand that of the vibration generator and on the other hand that of the pressure means.

With the configuration in accordance with the invention according to claim 4 the pressure production means have a pressure piston, acting on the filler mass, which can be acted upon pneumatically, wherein a common pressure supply is provided for a pneumatically drivable vibration generator and the pressure production means. Through this there is provided not only an effective and efficient drive but also a simple drive, because for both drive functions the common pneumatic pressure supply is available. In addition, the pneumatic pressure can be delivered by one or two pressure lines with simple construction.

The invention is further based on the object, with a hand apparatus according to the preamble of the claim 5, of extending the range of possible applications.

This object is achieved by the features of claim 5. Advantageous developments of the invention are indicated in associated dependent claims.

With regard to the configuration according to claim 5 the invention is based on the insight that in the case of a convention dental plaque removal device an energy release as required for the removal of plaque is present and this vibration energy is also suitable for dispensing the pasty filler mass.

With the configuration in accordance with the invention according to claim 5 the apparatus housing and the vibration generator are part of a convention dental plaque removal device with a vibrating tool tip, wherein the container with the pressure production means and the exit nozzle is fastenable to the tool. This configuration makes it possible to use the hand apparatus selectively as dental plaque removal device or as hand apparatus for dispensing the pasty filler mass. Thereby it is ensured, clue to the possibility of fastening the container containing the filler mass to the tool, that the vibration energy is transferable to the container. In addition, the container is located in a position in the forward region of the hand apparatus so that its exit nozzle also is in a position which is suitable for dispensing the pasty filler mass at the treatment site.

The invention is further based on the object of so configuring a container for receiving of a curable medical filler mass, that it is suitable for a hand apparatus for dispensing the pasty filler mass.

This object is achieved by the features of claim 18 or 20.

With the container in accordance with the invention according to claim 18 the container has a fastening element for axially and/or radially fixed connection with an oscillation part of a medical or dental-medical hand apparatus, wherein the container is of a reverberant material, in particular plastic.

With the configuration in accordance with the invention in accordance with claim 20 the container has a receiving body consisting of a hose section which at its ends is in each case is constricted by a closure.

In the case of both containers in accordance with the invention a good transfer of the vibration energy to the container is ensured. With the configuration in accordance with the claim 18 this is ensured by the presence of a fastening element and, further, ensured in that the container is made of a vibration-hard or reverberant material.

With the configuration according to the claim 20 this is ensured in that the container has a receiving body consisting of a hose section. With such a hose section the cross-sectional form and size thereof is flexible and therefore adaptable to the cross-sectional size of a receiving chamber receiving the hose bag. Thereby it is to be taken into account that the pressure which pressure production means present at a hand apparatus concerned exert on the hose bag, further improves the broad area bearing of the hose bag on the wall of the receiving chamber receiving it.

Figure 2:
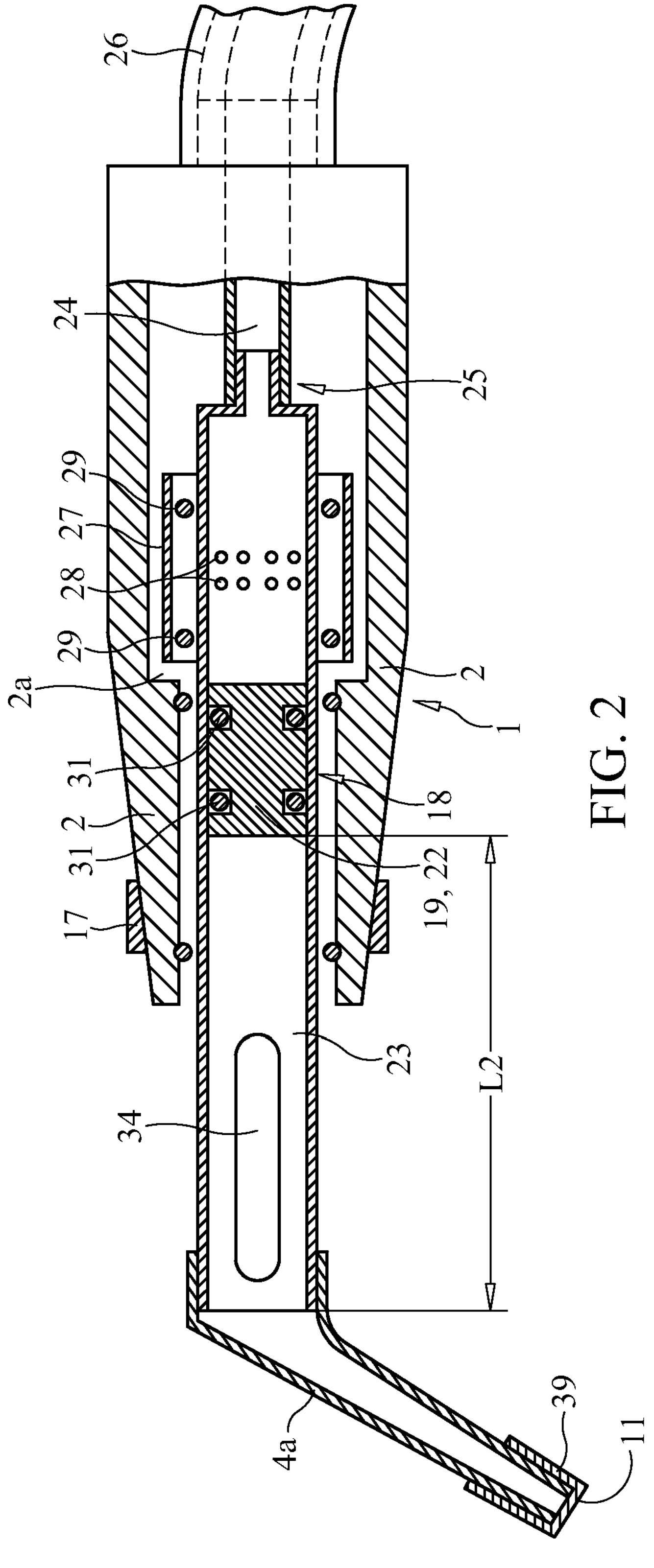
Figure 4:
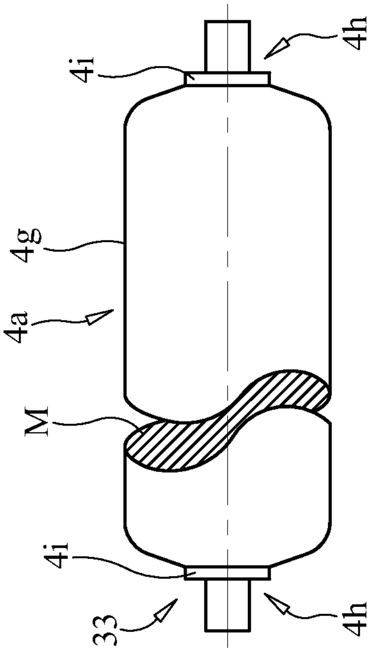
Figure 3:
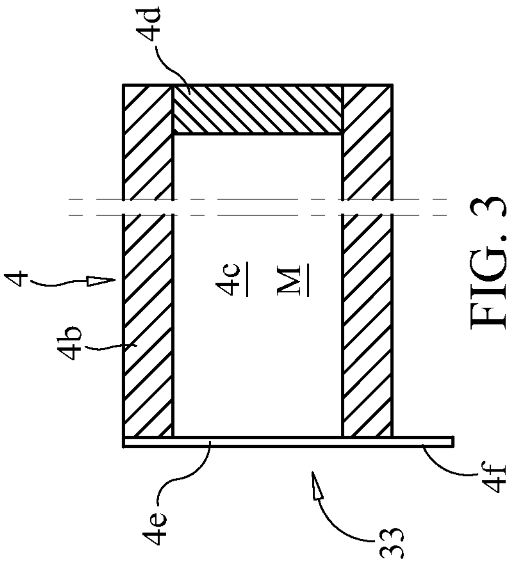
Figure 5:
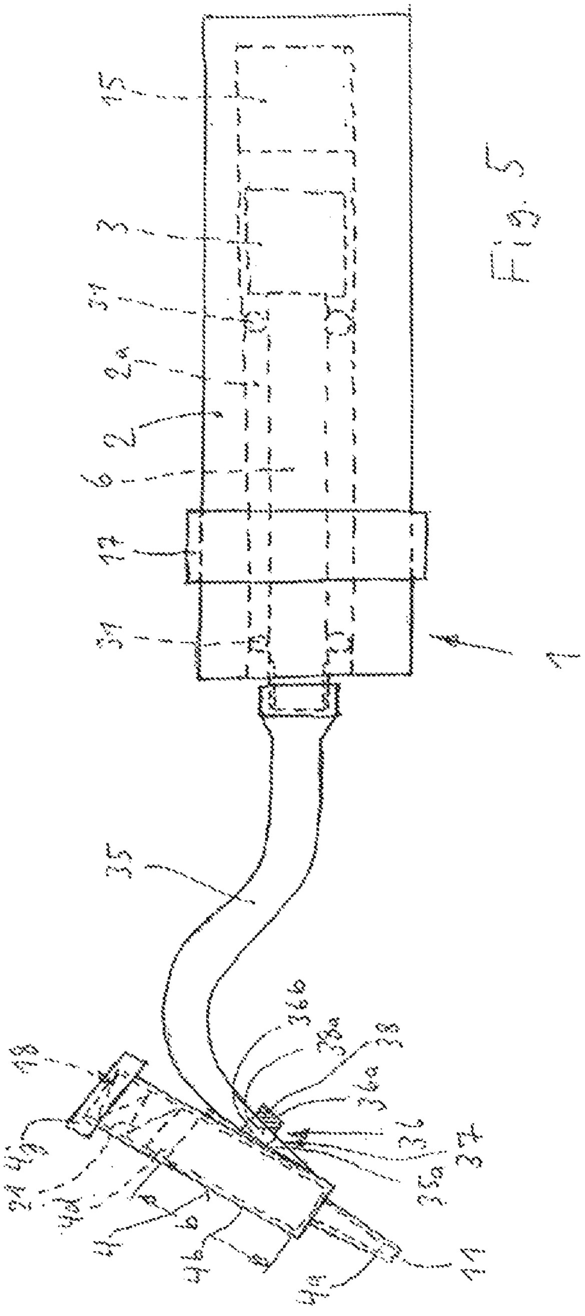

Below, advantageous configurations and developments of the invention are explained in more detail with reference to preferred embodiments and simplified drawings. There is shown:

FIG. 1 a hand apparatus in accordance with the invention, in longitudinal section;

FIG. 2 a hand apparatus in accordance with the invention in modified configuration, in longitudinal section;

FIG. 3 a further modified hand apparatus in accordance with the invention, in a side view;

FIG. 4 a container for the hand apparatus for receiving a pasty filler mass, in longitudinal section;

FIG. 5 a container in modified configuration, in a side view.

The main components of the hand apparatus designated as a whole by 1 are an elongate, in particular rod-shaped, and in the case of the embodiment straight extending, apparatus shaft 2, which at least in its forward region is formed hollow, preferably sleeve-like, and in which a vibration generator 3 is arranged, which generator stands in connection with a container 4 for receiving a pasty filler mass, the viscosity of which can be reduced by supply of oscillation energy, and will be further described below. The container 4 is firmly connected with the vibration generator 3 and therefore capable of taking up the vibration energy transferred to it from the vibration generator 3 and to execute vibrations. Here there may be involved vibrations whose amplitudes run in directions counter to one another, e.g. in the longitudinal direction of the shaft 2 or transversely thereto, or in many directions and therefore 3-dimensionally.

Thereby, the container 4 is mounted independently from the shaft forming an apparatus housing 5 for the vibration generator 3, so that it can also execute the vibrations independently of the housing 5 or shaft 4. This can be achieved in that the container 4 is firmly connected to an oscillation part 6 to which the vibration generator 3 transfers the vibration energy which it applies.

The oscillation part 6 is, in the case of the embodiment, an elongate oscillation shaft, extending longitudinally in the apparatus shaft 2 and with its forward end into the forward region of the apparatus shaft 2. The container 4 is preferably likewise constituted elongate and is connected with its rearward end, by means of a connection device 7, releasably with the forward end of the oscillation part 6. For this purpose the apparatus shaft 2 may have a receiving hole 8, through the forward opening of which the oscillation part 6 extends and for example projects forwardly beyond the apparatus shaft 2, or the oscillation part 6 can end before the forward end. In both cases the oscillation part 6 is, for connection with the container 4, accessible for this from the fore, so that the container 4 is connectable with the oscillation part 6, and thereby can be introduced, if applicable, through the opening 8.

To transfer the vibration power applied by the vibration generator 3 to the container 4 and the filler mass situated therein as far as possible in lossless manner, the connection device 7 has no play. This can be attained in that the connection parts, namely the oscillation part 6 and the container 4, bear on one another over a broad area in the longitudinal direction and transversely thereto, and fixedly in at least one direction. The connection device 7 is preferably a screw connection. In the case of the embodiment of FIG. 1, in which the container 4 can be introduced into and screwed into a receiving hole 9 of the oscillation part 6, the container 4 can bear with an approximately radial shoulder surface **7*a* on a counter-shoulder surface 7*b* of the oscillation part 6, and bear with a peripheral surface on a counter-peripheral surface of the oscillation part 6, under thread tension, and bear with its peripheral surface 7*c* on a counter-peripheral surface 7*d* of the oscillation part 6 formed by an inner surface of the hole 9. However, the rigid abutment can also be realised by means of axially inwardly convergent and matching conical surfaces on the outer periphery of the container 4 and on the inner periphery of the oscillation part 6, which ensure the rigid connection both in axial and also in radial direction. The container 4 has at its rearward end a rearwardly upstanding thread pin 7*c***, which can be screwed into the screw connection.

The container 4 can be formed by a sleeve body extending straight in the longitudinal direction, which has at its forward end an outlet opening 11 for the filler mass M. In order to improve the accessibility to the treatment site on the one hand ergonomically and on the other hand in consideration of a good view, the container 4 is formed in its forward end region as a forwardly tapering cannula **4*a*, which extends e.g. curved or straight, and with regard to the longitudinal middle axis 12 of the apparatus shaft 2 transversely, e.g. obliquely forwardly, and—seen longitudinally of the longitudinal middle axis 12—projects beyond the periphery of the apparatus shaft 2**.

The vibration generator 3 may be arranged at the rearward end of the preferably cylindrical and hollow oscillation part 6. It may be e.g. an electrical vibration generator 3, in particular a piezo vibration generator 3. There is, however, also excellently suitable a pneumatic vibration generator 3 which is operable with compressed air which can be delivered through a feed line which extends to the vibration generator 3 from the rear.

By means of a piezo vibration generator 3 vibrations can be produced the amplitudes of which have opposite directions, which run e.g. in the longitudinal direction of the longitudinal middle axis 12. Within the scope of the invention the direction oldie amplitudes may however also be transverse to the longitudinal middle axis 12, e.g. radially directed.

As FIG. 1 shows, the vibration generator 3 may be arranged between the oscillation part 6 and a counter oscillation part 13, which is likewise located in the hollow chamber **2*a* of the apparatus shaft 2, wherein the vibration generator 3 forms a connecting member connecting the oscillation part 6 and the counter oscillation part 13 with each other. For the radial mounting of the e.g. cylindrical oscillation part 6 there may be arranged in the apparatus shaft 2 an e.g. cylindrical receiving hole 8 in which the oscillation part 6 is mounted with a slight radial play for movement. For the axial positioning of the oscillation part 6, non-illustrated positioning elements are provided. In the region of the vibration generator 3 and in particular in the region of the counter oscillation part 13, the hollow chamber 2*a* of the apparatus shaft 2 is formed larger than the vibration generator 3 and/or the counter oscillation part 13**.

An energy source 15 may be arranged in the rearward region of the apparatus shaft 2, e.g. a battery, in particular an accumulator accessible from the outside for charging, which is connected by electrical lines with the vibration generator 3 and a control device, designated as a whole by 16, for changing and setting the vibration energy that can be transferred from the vibration generator 3 to the container 4 or the filler mass M. For changing the vibration energy the control device 16 has a movably mounted setting or control element 17, which may be part of a control apparatus external with respect to the hand apparatus 1 and may be arranged e.g. at a foot switch e.g. or may be movably mounted on the apparatus shaft 2. In the embodiment the control element 17 is arranged in the forward end region of the apparatus shaft 2 on the periphery thereof and movable longitudinally of the longitudinal middle axis 12 or transversely thereof, e.g. in the peripheral direction. Thereby, the control element 17 may be a ring element as FIG. 1 shows by way of example. By means of a movement and return movement of the control element 17 the transferable vibration energy can selectively be increased and reduced.

The filler mass M is a filler material for filling of cavities of the human or animal body, in particular a filler mass on synthetic resin basis, e.g. with a synthetic resin curable by ultraviolet light, as is know e.g. with dental filler masses M. To reduce a volume reduction of the filler mass M due to shrinkage upon hardening, the synthetic resin contains admixed inorganic materials e.g. in powder form. The higher the content of the filler mass M of such an inorganic material is, the greater is the toughness or viscosity of the filler mass M and the lesser is the shrinkage appearing upon hardening. By acting on the filler mass M with vibration energy the viscosity of the filler mass M is reduced so that it is able to emerge from the container 4 through the outlet opening 11 and to fill the cavity and also to fill out small corners of the cavity.

Thereby the control device 16 in accordance with the invention makes it possible not only to adapt the consistency or viscosity the filler mass M but also the quantity transported from the outlet opening 11 to local requirements e.g. to different forms and/or sizes of the cavity concerned. In order to fill a cavity of restricted cross-section or with small corners or gaps, the viscosity of the filler mass M can be reduced by an increase of the vibration power. In addition, the respectively desired transport quantity and therefore the filling procedure can be adjusted to local requirements. For large cavities the transport quantity can be increased and reduced for small cavities. With the embodiment of FIG. 1 it is advantageous to so adapt to each other the viscosity of the filler mass M, the pressure exerted by the pressure device 18 on the filler mass M, the vibration power and the size of the outlet opening 11 that with vibration generator 3 turned off the filler mass M does not leave the container 4 and therefore remains therein, and only with switched on vibration generator 3 emerges from the outlet opening 11 with a slight transport quantity, wherein this transport quantity can be selectively increased by an increase of the vibration power and again reduced.

The embodiment according to FIG. 2, in which the same or comparable parts are provided with the same reference signs, differs from the above-described embodiment in a number of respects.

Also in this embodiment the pressure device 18 is integrated into the oscillation part, whereby it has a pressure element 19 in the form of a pressure piston 22 which can be acted upon pneumatically, which bounds to the rear a receiving chamber 23 for the filler mass M arranged in the oscillation part 6 which chamber is forwardly open, and which can be acted upon at the rear with a pneumatic pressure. The pressure may be deliverable by a pneumatic pressure line 24 extending from the rear to the sleeve-like oscillation part 6, which e.g. is attached thereon at the rearward end of the oscillation part 6, e.g. by means of a line connection 25 which may be formed by a pipe or hose connection. In this embodiment the hand apparatus 1 is rearwardly connected, preferably by means of a flexible supply line 26, with a non-illustrated so-called supply apparatus which has a pressure source from which there extends the pressure line 24 longitudinally through the supply line 26.

In addition, in this embodiment there is preferably provided a pneumatic vibration generator 3 which is arranged behind the stroke region of the pressure piston 22 and can be formed by an oscillation sleeve 27 which surrounds the oscillation part 6 with a radial spacing, wherein in the longitudinal region of the oscillation sleeve 27 a plurality of radial holes 28 are arranged in the oscillation part 6. The oscillation sleeve 27 is positioned or limited in the longitudinal direction of the oscillation part 6 by suitable means. These may be formed by limitation rings 29 sitting axially fixedly on the oscillation part, which may be rings of an elastic material, e.g. plastic or rubber, sitting on the oscillation part 6 e.g. means of elastic clamping.

The pressure piston 22 is preferably sealed off in the oscillation part 6 by at least one e.g. two sealing rings 31 having an axial spacing from one another, wherein the sealing ring or rings 31 are in each case received in a ring groove in the pressure piston 22.

Also in this embodiment the vibration generator 3 can oscillate in vibration operation with amplitudes which are directed in mutually oppositely lying axial directions and/or radial directions of the oscillation part, wherein there may be involved a vibration generator 3 suitable for this, e.g. a piezo vibration generator or another vibration generator.

If a pneumatic vibration generator 3 is provided, mainly radial oscillation amplitudes are produced on the oscillation part 6 which, however, are also superposed by axial oscillation amplitudes so that 3-dimensional oscillation amplitudes result for the oscillation part 6. In response the oscillation part 6 can react with radial and also axial tilt movements, which with the embodiment in accordance with FIG. 2 are in particular therefore possible because the oscillation part 6 is mounted radially elastically yieldably in the apparatus shaft 2, e.g. by means of one or two bearing rings 32 having an axial spacing from one another, made of elastically compressible material, in particular rubber or plastic, of which the possibly present rearward bearing ring 32 is preferably arranged before the vibration generator 3. The bearing rings 32 can in each case be held in a ring groove which is e.g. located in the inner peripheral surface of the ring-like apparatus shaft 2. In this embodiment between the oscillation part 6 and the wall of the receiving hole 8 there is provided a radial play for movement, which makes possible the oscillation movements of the oscillation part 6.

It is possible, but not necessary and for reasons of a simple inspection advantageous, not to give the filler mass M directly into the receiving chamber 23, but to insert therein matching containers 4 filled with the filler mass M, so-called cartridges, out of which the filler mass M is forwardly pressable by a forwards movement of the pressure piston 22. These containers 4 therefore have at their forward ends an outlet opening 33 which is opened e.g. upon use in the receiving chamber 23 or opens automatically under the pressure applied by the pressure piston 22, e.g. at a weak point.

The container 4 can be slid from the fore into the sleeve-like oscillation part 6. In the embodiment in accordance with FIG. 2, in which a cannula **4*a* is connected releasably with the oscillation part 6, preferably by means of a screw connection, in particular by screwing on, the cannula 4*a* is released before an emplacement of the container 4 and thereafter again installed. The form of the cannula 4*a* can correspond to the construction described for the embodiment in accordance with FIG. 1**.

The oscillation part 6 may have, in front of the apparatus shaft 2, on one or on both sides, a preferably elongate viewing window 34, which makes it possible to recognise the capacity of the filler mass M, in particular with a configuration in form of a hose bag in accordance with FIG. 4.

With the embodiment in accordance with FIG. 2 the control element 17 can serve to act on the vibration generator 3 and the pressure piston 22 at the same time and together with the pressure fluid of the pressure line 24. An in this case associated common valve in the pressure line 24 can be arranged in the region of the hand apparatus 1 or in the region of the above-described non-illustrated supply apparatus.

In the case of the embodiment in accordance with FIG. 2 the viscosity of the filler mass M is preferably so great, under consideration of the cross-sectional size of the outlet opening 11, that with pressure device 18 not switched on and vibration generator 3 not switched on it does not run out through the outlet opening 11 from the container 4 or the cannula **4*a* and therefore remains in the oscillation part 6**.

Within the scope of the invention the viscosity can be so great that with pressure device 18 switched on the filler mass M is pressed out through the outlet opening 11. The pressure device 18 can therefore be used for the purpose of transporting the filler material M out of the apparatus shaft 2. By means of a vibration generator 3 which can be additionally switched in the viscosity can then be reduced and the transport quantity increased. If, beyond this, the vibration power of the oscillation generator 3 is adjustable, namely can be increased and again reduced, the viscosity can be reduced further and again increased, and the transport quantity increased and again reduced.

In the case of all embodiments in accordance with FIGS. 1 to 3 the container 4 has a peripheral wall **4*b*, which at least in a rearward longitudinal section surrounds a prismatic, in particular cylindrical receiving chamber 4*c*, which is closed by a piston cover 4*d***, inserted from the rearward end, of suitable cross-sectional form.

In the case of the embodiment according to FIG. 3 the perimeter wall **4*b* is a hollow cylindrical wall which is closed at its forward end by a thin end wall 4*e*, in particular a foil, e.g. of metal or plastic. The end wall 4*e* can e.g. be adhered together with the end face of the perimeter wall 4*b*. At least one side the end wall 4*e* can project laterally beyond the perimeter wall of 4***b*. A so formed grip edge 4*f* can serve to tear off the end wall 4*e* and thus to open the container 4 at its forward end, for use. An opening can however also be created in that the end wall is pierced through. This can also be effected with a container 4 and hose bag in accordance with FIG. 4.

The outer cross-sectional dimension of the perimeter wall 4*b* is adapted, under consideration of an adequate play for movement, to the cross-sectional dimension of the in this case cylindrical receiving hole 9, so that the container 4 can be inserted therein from the fore.

In the case of the embodiment according to FIG. 4, in which the same or comparable parts are likewise provided with the same reference signs, the container 4 is formed by a hose bag 4*g*, which is closed at one or at both ends by a closure 4*h*, which may be formed by a ring-like constriction part 4*i*, which surrounds an end section of the hose of the hose bag 4*g* and presses it together in the sense of a constriction. Also in the case of this embodiment the cross-sectional form and dimension of the hose bag 4*g* is so adapted with play for movement to the cross-sectional dimension of the receiving hole 9 that the hose bag 4*g* can be inserted into the oscillation part 6 in accordance with FIG. 2. Due to the pliability of the pasty filler mass M the cross-sectional dimension of the hose bag 4*g* can also be slightly greater. Since the hose bag 4*g* allows itself to be pressed together transversely, it is adaptable to the cross-sectional dimension of the receiving hole 9.

In the case of the embodiment according to FIG. 1 the length L1 of the straight extending longitudinal section of the receiving chamber 4*c* or of the straight extending rearward longitudinal section of the peripheral wall 4*b* is adapted to the depth of the receiving hole 9. In the case of the embodiments according to FIGS. 3 and 4 the total lengths of the containers 4 are adapted to the available length L2 of the receiving chamber 23 in the oscillation part 6, which is predetermined by the spacing of the pressure piston 22 from the forward end of the sleeve-like oscillation part 6.

Unlike usual cartridges known for joint sealing apparatuses, in the case of the container 4 in accordance with the invention the perimeter wall 4*b* is not only considerably thicker, but it also consists of a reverberant material which is well suited for a transmission of body-carried noise through the peripheral wall 4*b* to the filler material. The piston cover 4 also consists this of such a material. As such a reverberant material there is well suited a metal, in particular light metal such as aluminium, or plastic, because of a desired slight weight.

In the case of the embodiment according to FIG. 5, in which the same or comparable parts are likewise provided with the same reference signs, the hand apparatus 1 is a dental plaque removal device known per se, as is described e.g. in DE 100 39 198 A1. The main parts of this known hand apparatus 1 are likewise an e.g. straight extending apparatus shaft 2 in which a rod-shaped oscillation part 6 is mounted so as to be capable of oscillation, e.g. likewise by means of rings 31 made of elastic material, such as rubber or plastic. A vibration generator 3 is arranged in an associated hollow chamber 2*a* of the apparatus shaft 2, whereby it acts on a rearward longitudinal section of the oscillation part 6, e.g. is fastened thereto or is integrated into the oscillation part. This hand apparatus 1 has an elongate operating tool 35, extending in substance forwardly from the oscillation part 6, e.g. in form of a hooked-shaped curved spur, which in case of the embodiment is formed in its forward end region conically forwardly convergently.

In the case of this hand apparatus 1 the container 4 containing the filler mass M and having a pressure device 18 is fastened releasably in the forward end region of the operating tool 35 by means of a releasable fixing device 36. This includes a fastening part 36*a* arranged on the container 4 and a corresponding fastening part 36*b* on the operating tool 35, which as parts of the fixing device 36 are fastenable to each other, preferably in the manner of a quick fastening connection, which can be brought about in handling friendly and rapid manner, and again released.

In the case of the present embodiment the fixing device 36 is formed by a clamping device exploiting the wedge effect of the convergent conical end region 35*a* of the operating tool 35. The fastening part 36*a* associated with the container 4 is preferably arranged in the middle longitudinal region of its outer perimeter and formed e.g. by an insertion recess 37 convergent towards the forward end of the container 4, which is so adapted to the cross-sectional form and size of the forward end region 35*a* of the operating tool 35 that the container 4 with its fastening part 36*a* can be inserted onto the operating tool 35 in clamping manner. The insertion recess 37 may e.g. be formed by a bow 38 fastened to the outer periphery of the container 4, the inner surface 38*a* of which is so adapted to the cross-sectional size and convergence of the operating tool 35 that it is clampable or fastenable by insertion.

In the case of the embodiment according to FIG. 5 the pressure device 18 can be formed by the spring 21 and the pressure piston or piston cover 4*d* displaceably guided the hollow cylindrical peripheral wall 4*b*. The compression spring 21 may bear on a rear cover 4*j* of the container 4, which is connected by a quick fastening connection, e.g. a bayonet connection or a screw connection, with the rearward end of the container 4 or of the peripheral wall 4*b*. The compression spring 21, preferably formed by a coil spring, can obtain its biasing in that its length in the relaxed condition and in the initial position of the piston cover 4*d*, in the container 4 filled the filler mass M, projects beyond the rearward end of the container 4, and through the closing of the cover 4*j* is so far pressed together axially and biased, that this biasing suffices for the pressure stroke of the piston cover 4 indicated by b in FIG. 5 this also stands in its forward stroke position under the biasing of the compression spring 21.

In the case of all embodiments it is advantageous to close the outlet opening 11 by a closure, which can be formed e.g. by a closure cap 39 which is e.g. inserted releasably onto the forward end of the container 4 constituted as a cannula of 4*a*.

The invention claimed is:

1. A dental handgrip for delivering filling compound into a tooth cavity at a treatment site comprising:

a connection device, to which a filling compound container is connectible, a fluid-operated feeding device operable to feed the filling compound from the filling compound container when the filling compound container is connected to said connection device; and a fluid-actuated vibration generator to selectively transmit vibrations to the filling compound to assist in feeding the filling compound to the treatment site, said fluid-actuated vibration generator being arranged in the handgrip, so that the vibrations generated by the vibration generator can be transmitted up to a delivering opening from which the filling compound is delivered to the treatment site, and wherein the handgrip is designed such that fluid which actuates the vibration generator does not suck the filling compound out of the filling compound container.

2. The dental handgrip according to claim 1, further comprising: a coupling element for the connection of the feeding device to an external fluid source.

3. The dental handgrip according to claim 1, wherein the feeding device comprises a feeding element displaceable by the fluid in the direction of the connection device, wherein the feeding element is configured to push filling material out of the filling compound container.

4. The dental handgrip according to claim 3, wherein the vibration generator and the displaceable feeding element are connected to one another directly or indirectly, so that at least a part of the fluid can be used for the operation of the displaceable feeding element and the vibration generator.

5. The dental handgrip according to claim 4, wherein a common fluid line is provided for the vibration generator and the displaceable feeding element.

6. The dental handgrip according to claim 3, wherein the vibration generator comprises a hollow vibration shaft, through the interior space whereof a fluid portion driving the displaceable feeding element can be routed to the displaceable feeding element.

7. The dental handgrip according to claim 6, wherein the vibration shaft emerges into a chamber, in which at least a part of the feeding device is disposed.

8. The dental handgrip according to claim 1, wherein the fluid-actuated vibration generator is operatively coupled to the connection device to transmit vibrations via the connection device to the filling compound, said connection device being arranged at a front end of the handgrip, the front end being near the delivering opening.

9. A dental handgrip for delivering filling compound into a tooth cavity at a treatment site comprising:

a connection device, to which a filling compound container is connectible, a fluid-operated feeding device operable to feed the filling compound from the filling compound container when the filling compound container is connected to said connection device; and a fluid-actuated vibration generator to selectively transmit vibrations to the filling compound container to assist in feeding the filling compound to the treatment site, said fluid-actuated vibration generator being arranged in the handgrip.

* * * * *